(12) United States Patent
Barnhizer et al.

(10) Patent No.: US 10,844,442 B1
(45) Date of Patent: Nov. 24, 2020

(54) RAPID VIRAL ASSAY

(71) Applicants: Bret T. Barnhizer, Poland, OH (US); Jonathan P. Faro, Bellaire, TX (US)

(72) Inventors: Bret T. Barnhizer, Poland, OH (US); Jonathan P. Faro, Bellaire, TX (US)

( * ) Notice: Subject to any disclaimer, the term of this patent is extended or adjusted under 35 U.S.C. 154(b) by 0 days.

(21) Appl. No.: 16/876,184

(22) Filed: May 18, 2020

(51) Int. Cl.
| | | |
|---|---|---|
| *A61K 39/00* | (2006.01) | |
| *C07K 14/005* | (2006.01) | |
| *A61K 39/12* | (2006.01) | |
| *A61K 39/145* | (2006.01) | |
| *C12N 7/00* | (2006.01) | |
| *C12Q 1/70* | (2006.01) | |
| *C12Q 1/6804* | (2018.01) | |

(52) U.S. Cl.
CPC ........... *C12Q 1/701* (2013.01); *C12Q 1/6804* (2013.01); *C12Q 2600/112* (2013.01)

(58) Field of Classification Search
CPC ....... A61K 39/12; A61K 39/145; A61P 31/16; C07K 14/005; C12N 2760/16134
See application file for complete search history.

*Primary Examiner* — Barry A Chestnut
(74) *Attorney, Agent, or Firm* — Acker Wood IP Law LLC; Gwen R. Acker Wood

(57) ABSTRACT

The invention provides a method for rapid, highly specific and sensitive detection and quantification of a virus by observing viral substrate binding to its host receptor protein. The invention also provides a method for rapid, highly specific and sensitive detection and quantification of a virus in an individual suspected of being infected with a virus. The invention further provides a test kit for rapid, highly specific and sensitive point-of-care detection of a virus in an individual. The viruses and their host receptor proteins that can rapidly be detected include SARS-CoV-2 and its host receptor protein ACE2. The surprisingly rapid, specific and sensitive method of the invention provides a point-of care test capable of diagnosing individuals suffering from COVID-19 by observation of a color change in the assay, which color change occurs in about five minutes, and which test can be completed by a user in about one hour.

25 Claims, 2 Drawing Sheets

RAPID VIRAL ASSAY

FIELD OF THE INVENTION

The invention relates to a rapid, highly specific and sensitive viral assay for the detection and quantification of various classes of viruses and, in particular, to a rapid, highly sensitive and specific viral assay for rapid detection and quantification of coronavirues, such as the novel coronavirus, SARS-CoV-2, which is responsible for COVID-19, as well as a point-of-care test kit for rapid, sensitive and specific detection of SARS-CoV-2.

BACKGROUND OF THE INVENTION

In December of 2019, three individuals in Wuhan, China, were noted to have developed pneumonia of uncertain cause. Two of the individuals made a full recovery; the third succumbed to the infection and died. Researchers were able to isolate a novel coronavirus, named Severe Acute Respiratory Syndrome Coronavirus 2 (SARS-CoV-2), and showed that this was the causative agent for these infections and subsequent disease, referred to as COVID-19. SARS-CoV-2 contains a single-strand of positive-sense RNA, which is 29,727 nucleotides in length, and contains five well-described open reading frames (ORFs). These ORFs code for the structural and non-structural proteins necessary for replication of the virus. SARS-CoV-2 shows significant homology to other coronaviruses, such as SARS-CoV and MERS-CoV (all members of the betacoronaviruses family, which are known to infect mammals), and has been found to share 88% to 96% sequence homology with a SARS-like coronavirus known to infect bats.

While the number of infected individuals has increased exponentially since those first three cases, testing for the presence of SARS-CoV-2 has remained problematic. Testing protocols have varied from country to country, with each providing its own recommendations. The World Health Organization (WHO) has clearly recommended that all individuals who need testing be tested, whereas the Centers for Disease Control (CDC) explicitly has stated that not everyone should receive testing. Initial recommendations from the WHO on testing individuals infected with the virus focused entirely on nucleic acid amplification technology (NAAT), which includes reverse transcriptase polymerase chain reaction (RT-PCR) tests, and the CDC quickly followed suit. After several missteps with regard to how tests were being performed, and who could perform the tests, the FDA loosened its restrictions and allowed many private companies to produce independent versions of the test. As of Apr. 23, 2020, there have been thirty-two FDA-approved COVID-19 testing kits. In addition to relaxing their restrictions on companies licensing these tests, the FDA also loosened their previous requirement that tests focus on two separate segments of the viral genome. Indeed, the recently approved Abbott ID NOW' COVID-19 Assay tests only for a single viral gene and a RNA-dependent RNA polymerase (RdRP).

With strong urging by the public as well as healthcare providers to offer more testing, the FDA has continued to open up the market to additional assay development. On Apr. 28, 2020, the FDA issued an Emergency Use Authorization for SARS-CoV-2 antibody tests (lateral flow immunoassays). The use of serology has been proposed to serve in a different capacity than RT-PCR; positive serology results indicate that an individual may have recovered from COVID-19 infection and, importantly, may imply that the individual has developed immunity against re-infection.

The primary problem with the approach of using RT-PCR to diagnose COVID-19 infection, and serology to indicate immunity to the ongoing COVID-19 pandemic, is that these tests are not well-suited to answer the primary question: is a specific individual presently infected with SARS-CoV-2? Although powerful, RT-PCR is costly, time-consuming, requires sophisticated equipment, has inherent false-positive and -negative results, and is better equipped to provide answers to questions related to how certain viral clades arise and spread through distinct regions.

Thus, the shortcoming with respect to SARS-CoV-2 detection in an individual is that when RT-PCR provides a positive result, it does not indicate that the virus is intact, viable, or infectious. It merely shows that the specific target gene has been detected. Furthermore, in cases where mutations occur at a high rate, which is known to occur with RNA viruses such as coronaviruses, RT-PCR runs the risk of overlooking the virus if a gene mutation occurs within the targeted amplification region.

Serology testing also has its limitations. While detection of IgM and IgG antibodies imply that an individual's immune system is mounting a defense against a specific pathogen, the progression from IgM to IgG is purely a correlation; we do not yet know enough to say that the development of a robust antibody response will confer immunity to a virus. In fact, there are well-described examples in which the development of an antibody response either fails to provide lasting protection, or in fact leads to worsening disease when re-exposure occurs.

Indeed, it bears mentioning that never before has the approach been taken of using RT-PCR and serology to control a spreading pandemic. These tests primarily are the tools of the epidemiologist, not the clinician. Rather, what is urgently needed is a test that can rapidly and accurately determine not only that a viral pathogen is present, but whether that pathogen is intact and possibly still infectious.

SUMMARY OF THE INVENTION

The present invention fulfills this need by providing a diagnostic method for rapid, highly specific and sensitive, detection and quantification of a virus, such as SARS-CoV-2, which causes COVID-19 disease. The method comprises the steps of coating a plurality of microtiter wells in a microtiter plate with a host receptor protein contained in a coating buffer; incubating the plurality of microtiter wells overnight; washing the microtiter wells; adding a blocking solution to the plurality of microtiter wells; washing the plurality of microtiter wells three times; adding a viral substrate to the plurality of microtiter wells; incubating the plurality of microtiter wells for 20 minutes; washing the plurality of microtiter wells three times; adding an antibody directed against the viral substrate to the plurality of microtiter wells; incubating the plurality of microtiter wells for 20 minutes; adding a horseradish peroxidase (HRP)-conjugated antibody directed against the anti-viral substrate antibody to the plurality of microtiter wells; incubating the plurality of microtiter wells for 20 minutes; washing the plurality of microtiter wells three times; adding a TMB solution to the plurality of microtiter wells; adding a stop solution to the plurality of microtiter wells; and detecting the viral substrate in the microtiter wells by observing those microtiter wells that undergo a color change, or quantifying the concentration of the viral substrate by reading optical density at 450 nm, wherein color change is observed in about five minutes and the method is completed by a user in about one hour.

In another aspect of the present invention, there is provided a diagnostic, point-of-care method for rapid, highly specific and sensitive, detection and quantification of a virus from an individual suspected of being infected with a virus. The method comprises the steps of coating a plurality of microtiter wells with a host receptor protein contained in a coating buffer; incubating the plurality of microtiter wells overnight; washing the microtiter wells; adding a blocking solution to the plurality of microtiter wells; washing the plurality of microtiter wells three times; adding a viral substrate, the viral substrate obtained via a specimen collected from an individual suspected of being infected by a virus or possibly exposed to someone infected with a virus, to the plurality of microtiter wells; incubating the plurality of microtiter wells for 20 minutes; washing the plurality of microtiter wells three times; adding an antibody (i.e., primary antibody) directed against the viral substrate to the plurality of microtiter wells; incubating the plurality of microtiter wells for 20 minutes; adding a horseradish peroxidase (HRP)-conjugated antibody (i.e., secondary antibody) directed against the primary antibody to the plurality of microtiter wells; incubating the plurality of microtiter wells for 20 minutes; washing the plurality of microtiter wells three times; adding a TMB solution to the plurality of microtiter wells; adding a Stop solution to the plurality of microtiter wells; and detecting the viral substrate in the microtiter wells by observing those microtiter wells that undergo a color change, or quantifying the concentration of the viral substrate by reading optical density at 450 nm, wherein the color change is observed about five minutes and the method is completed by a user in about one hour.

In both the above-described methods, after adding a blocking solution to the microtiter wells, the microtiter plate may be stored, after which it can be shipped for use to another site, as the assay start time begins only when the viral substrate is added to the microtiter wells.

The host receptor protein may be, without limitation, ACE2; the viral substrate may be, without limitation, a SARS-CoV-2 Spike protein or a recombinant Spike protein; and the suspected virus may be, without limitation, SARS-CoV-2.

The primary antibody may be, without limitation, a rabbit polyclonal antibody directed against the SARS-CoV-2 Spike protein or the recombinant Spike protein; and the HRP-conjugated antibody directed against the primary antibody may be, without limitation, an HRP-conjugated anti-rabbit polyclonal goat antibody. Tags other than HRP directed against the primary antibody may be used in the invention, including, without limitation, alkaline phosphatase, His, FLAG, or a fluorescent tag. The invention contemplates that any antibodies used, whether they are primary or secondary antibodies, can be either polyclonal or monoclonal, IgG, or IgM, and may be derived from any suitable antibody-producing animal.

The specimen obtained from the individual suspected of being infected by a virus may include, without limitation, a nasopharyngeal swab, cerebrospinal fluid, amniotic fluid, serum, plasma, whole blood, bronchopulmonary lavage, nares, vaginal sampling, semen, or rectal/stool sampling.

In a further aspect of the invention, there is provided a test kit for rapid, highly specific and sensitive, point-of-care detection of a virus from an individual suspected of being infected with the virus. The test kit comprises a plurality of microtiter wells in a microtiter plate, the microtiter wells coated with a host receptor protein specific for the virus deposited on surfaces of the plurality of microtiter wells; a primary antibody directed against the viral substrate; a wash liquid for washing the plurality of microtiter wells and for preparing a mixture consisting of the wash liquid, an HRP-conjugated secondary antibody directed against the primary antibody and a specimen obtained from an individual suspected of being infected with the virus, said mixture made into one or more serial dilutions which are deposited atop the coating in the plurality of microtiter wells; a TMB solution; and a STOP solution, wherein the detection of the virus in the specimen is achieved by observing those microtiter wells that undergo a color change, wherein the color change is observed in about five minutes and the test is completed by a user in about thirty minutes.

BRIEF DESCRIPTION OF THE DRAWINGS

A fuller understanding of the invention can be gained from the following description when read in conjunction with the accompanying drawings, in which.

DETAILED DESCRIPTION OF THE INVENTION

Figure 1:
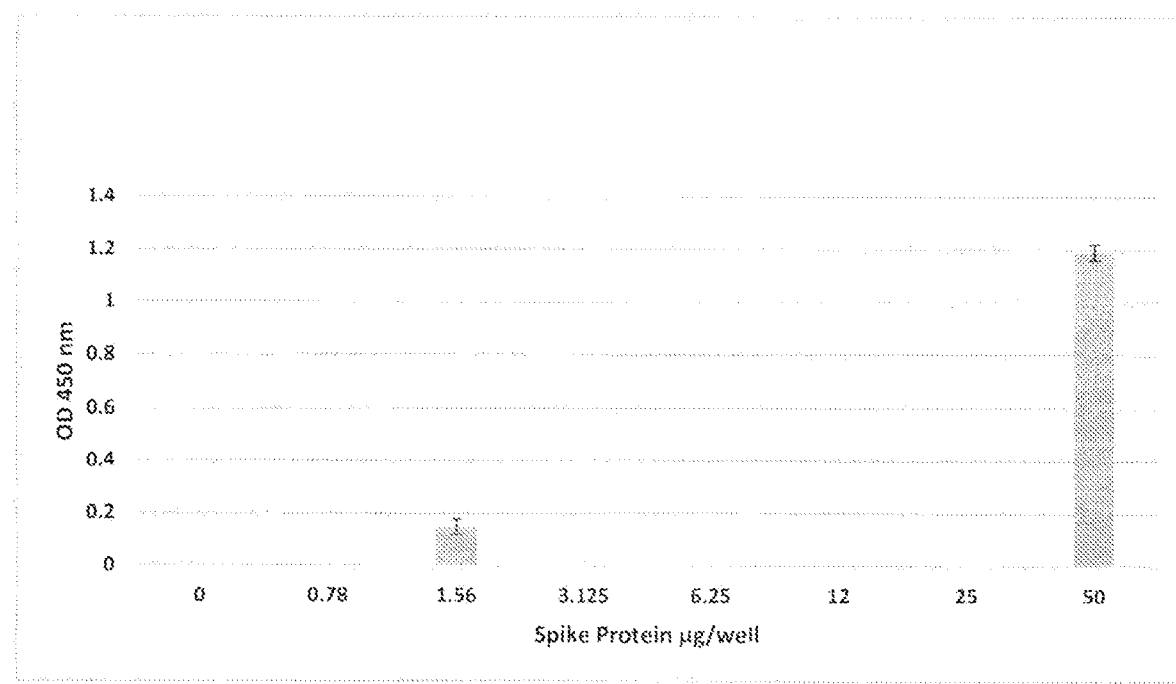
FIG. 1 is a bar graph showing detection of two different concentrations of a SARS-CoV-2 Spike protein using arbitrary dilutions of a polyclonal rabbit anti-Spike antibody and an HRP-conjugated goat anti-rabbit antibody, which illustrates the surprising specificity of the invention.

As used herein, "host cell receptor," "host receptor protein," viral host receptor protein" and "ligand" are meant to be interchangeable.

As used herein, "COVID-19," "SARS-CoV-2," and "novel coronavirus" are meant to be interchangeable.

As used herein, "infection" and "disease" is meant to be interchangeable.

As used herein, "a user" is defined as an individual that wishes to determine whether he/she, or some other individual, is infected with a virus, such as the SARS-CoV-2 virus. Thus, a user includes, without limitation, front-line workers such as EMT technicians, police officers, firemen, health care workers, doctors or nurses, or any other individual wishing to determine viral status for themselves or others.

In an embodiment of the present invention, there is provided a rapid, highly specific and sensitive assay that demonstrates the interaction between a virus and its cellular receptor protein. This interaction may be shown in various classes of viruses, including, without limitation, severe acute respiratory syndrome coronavirus 2 (SARS-CoV-2), human immunodeficiency virus (HIV), respiratory syncytial virus (RSV) and human papilloma virus (HPV).

Some representative examples of classes of viruses and their receptor proteins that may be rapidly assayed by the present invention include, without limitation, SARS-CoV-2:Spike protein and ACE2; SARS-CoV-2:Spike protein and other host protein candidates; Betacoronaviruses (lineage A):Hemagglutinin esterase and sialic acid receptors; Influenza:Hemagglutinin protein, sialic acid receptors and HA2; Murine hepatitis virus (MHV):Spike protein and carcinoembryonic antigen-related cell adhesion molecule 1 (CEACAM1); and Middle East respiratory syndrome (MERS):Spike protein and dipeptidyl peptidase 4 (DPP4/CD26).

In this embodiment, the rapid viral assay comprises the following steps. First, a host receptor protein contained in a coating buffer, which is chosen based on previous studies, or selected from a panel of protein candidates, is used to coat microtiter wells at various concentrations. In addition to proteins, other molecules may be used, including, without limitation, aptamers, affimers, polysaccharides, DNA/RNA, and the like. Next, a viral substrate is added at various concentrations. The viral substrate can include, without limitation, a purified viral protein, a purified, recombinantly-generated viral protein, or intact virus-live-attenuated, heat-killed viable virus, or a virus-like particle. Purified, recombinantly-generated viral proteins and virus/virus-like particles can include, without limitation, a Spike protein, a nucleocapsid protein, an envelope protein, an RNA-dependent RNA polymerase (RdRP)-protein for SARS-CoV2 or a hemagglutinin esterase for influenza. After washing, any remaining viral substrate that still is bound to the coating antigen then is detected with a primary antibody directed against the viral substrate and an HRP-conjugated secondary antibody directed against the primary antibody.

With the use of this assay, the quality of the binding can be studied by changing the biological matrix, salt concentration and/or adding detergents, so that hydrophilic/hydrophobic interactions may be assessed. Furthermore, additional molecules may be added immediately before, during and after the viral substrate is added in order to determine the nature of the binding. By focusing on the interaction between the virus and its receptor protein, i.e., ligand, various chemicals/therapeutic candidates, such as anti-viral monoclonal/polyclonal antibodies, antibody purified from convalescent sera, hydroxychloroquine, chloroquine, or remdesivir, may be added into the assay, and any effect from the chemical/therapeutic candidate on either the cellular receptor protein/ligand or virus may be ascertained.

In another embodiment of the present invention, there is provided a rapid assay which can determine if an intact virus has been isolated. This may provide insight as to whether an individual has an infection, and if the infectious agent still is intact. This provides essential information to clinicians, as intact virions are a prerequisite for transmission of viral disease. PCR or RT-PCR testing is unable to make this distinction between viable and non-viable viruses, and serology studies, i.e., determination of the presence of IgM/IgG antibodies in serum, also are unable to make this distinction.

In this embodiment, the rapid viral assay comprises the following steps. First, microtiter wells are coated with a viral host receptor protein candidate, such as, without limitation, ACE2, which is the receptor protein for SARS-CoV-2. After blocking, a virus is added. After washing with PBS/PBS-Tween, an antibody directed against either the envelope (E) protein, membrane (M) protein, or Spike (S) protein of the virus is added, an antibody then is added, after which an HRP-conjugated antibody directed against the antibody is added, and any bound, intact virions are identified.

While this assay is able to detect intact virions, it is possible that these virions may not be infectious, i.e., they are empty virions or remnants of viral particles. Thus, in a further embodiment of the present invention, there is provided a rapid assay which can serve as a test to determine if an intact, infectious virus has been isolated.

In this embodiment, the rapid viral assay comprises the following steps. First, microtiter wells are coated with a viral host receptor protein candidate. After blocking, a virus is added. After washing with a viral lysis buffer, an antibody directed against a nucleocapsid protein, or an RNA-dependent RNA Polymerase (RdRP) protein complex, is added.

Next, the liquid from these wells is transferred to wells which are coated with antibody against the same protein (i.e. anti-nucleocapsid/RdRP complex antibody). This pulls down and captures non-structural viral proteins. Importantly, it is necessary to use a capture antibody (i.e., a primary antibody) of a specific species, for example, a rabbit, and a detection antibody (i.e., secondary antibody) from a different species, for example, a goat, as an additional HRP-labeled antibody directed specifically against the detection antibody, may be needed.

The present invention therefore provides a unique approach of focusing on the interaction between a virus and its host-cell receptor. By "pulling down" the virus and capturing it onto receptor-coated wells, it allows for an entirely new set of questions to be answered. In using this approach, the target antigen used for detection can be changed, so that an entirely different component of the virus may be detected. For example, if an intact virion binds to ACE2-coated wells through the Spike protein, then distant envelope proteins within the viral membrane may be detected. In addition, bound virus may be lysed, allowing the release and detection of genomic material/nucleocapsid/RdRP.

Utilization of this novel approach may allow for the more accurate determination of infectivity. One of the main drawbacks of PCR and RT-PCR is that viral genomic material may be isolated days to weeks after infection has resolved, which is less likely when antigen-binding assays are utilized. This is an incredibly important distinction to make when employers are requiring their employees to have negative test results before returning to work. The present invention thus provides the ability for individuals suspected of being infected with the virus to provide a sample, and if this sample contains intact virus with functional Spike protein (judged to be functional by its ability to bind to its host-cell receptor), then that individual most likely still is contagious.

In addition, focusing on the interaction between the Spike protein and the host cell receptor allows one to study the influence that certain therapeutic candidates have on the SARS-CoV-2 virus. If, for instance, hydroxychloroquine negatively influences the binding of the viral Spike protein to its host cell receptor, then this may prove to be a beneficial relationship to exploit in treating those infected/exposed to the virus. Determining the nature of this relationship may also aid in determining which individuals who have recovered from infection have developed neutralizing antibodies. By purifying antibodies from these individuals, one can determine that certain individuals have produced an antibody response that more effectively targets the virus. Finally, this also may prove to be useful for vaccine manufacturers.

EXAMPLES

The present invention is more particularly described in the following non-limiting example, which is intended to be illustrative only, as numerous modifications and variations therein will be apparent to those skilled in the art.

Example 1—Rapid Binding Assay of ACE2 and SARS-CoV-2 Spike Protein to Detect COVID-19

Two experiments were conducted to observe the rapidity, specificity and sensitivity of the methods of the invention for detecting and quantifying viruses, as well as to set negative and positive controls for these methods.

In the first experiment, microtiter wells (Immulon, ThermoFisher, Waltham, Mass.) were coated with 100 µl of 1 µg/well of ACE2 (RayBiotech #230-30165-100) in bicarbonate buffer (Sigma, St. Louis) and incubated overnight at 4° C. The wells were washed and then blocked with 200 µl/well StartingBlock™ (ThermoScientific, Rockford, Ill.). Wells were washed three times with phosphate-buffered saline (PBS, Sigma Aldrich, PA) supplemented with 0.05% Tween-20 (PBS-Tw; Fisher Scientific, Pittsburgh, Pa.) at room temperature. Next, serial dilutions of Spike protein (SARS-CoV-2 Spike protein recombinant S1 subunit purchased from RayBiotech, #230-01101) in PBS were added to the wells, starting at a concentration of 50 µg/well, and diluting out to 0.8 µg/well. Wells were incubated for 20 minutes at room temperature, and then washed three times with PBS-Tw. Next, rabbit polyclonal antibody (GeneTex #GTX135356) directed against SARS-CoV-2, diluted 1:100 in PBS was added, 100 µl/well, and incubated at room temperature for 20 minutes. Wells were again washed three times with PBS-Tw, and then HRP-conjugated anti-rabbit polyclonal goat antibody (Sigma Aldrich) diluted 1:2,000 in PBS was added, 100 µl/well, and incubated for 20 minutes at room temperature. Wells were again washed three times with PBS-Tw. TMB peroxidase substrate (Sigma Aldrich) then was added, 100 µl/well. Within 10 minutes, 100 µl/well Stop Solution (Thermo Scientific) was added, and ODs were measured at 450 nm on a BIO-RAD iMARK microplate reader.

As an alternative to reading the OD at 450 nm, a visual, qualitative detection of Spike protein was able to be made within 1-2 minutes after the addition of TMB, i.e., without the use of the microplate reader, by observing a color change in the microwells. Microwells that changed from light blue to dark blue in color indicated the presence of the Spike protein. This color change was fully-observable in about five minutes after adding TMB.

FIG. 1. shows the detection of two different concentrations of Spike protein. In addition to testing the concentration of Spike protein, arbitrary dilutions of polyclonal anti-Spike antibody, and HRP-conjugated anti-rabbit antibody were also selected (1:100 and 1:2,000, respectively). A surprisingly high specificity for Spike protein of at least 98% was observed.

Figure 2:
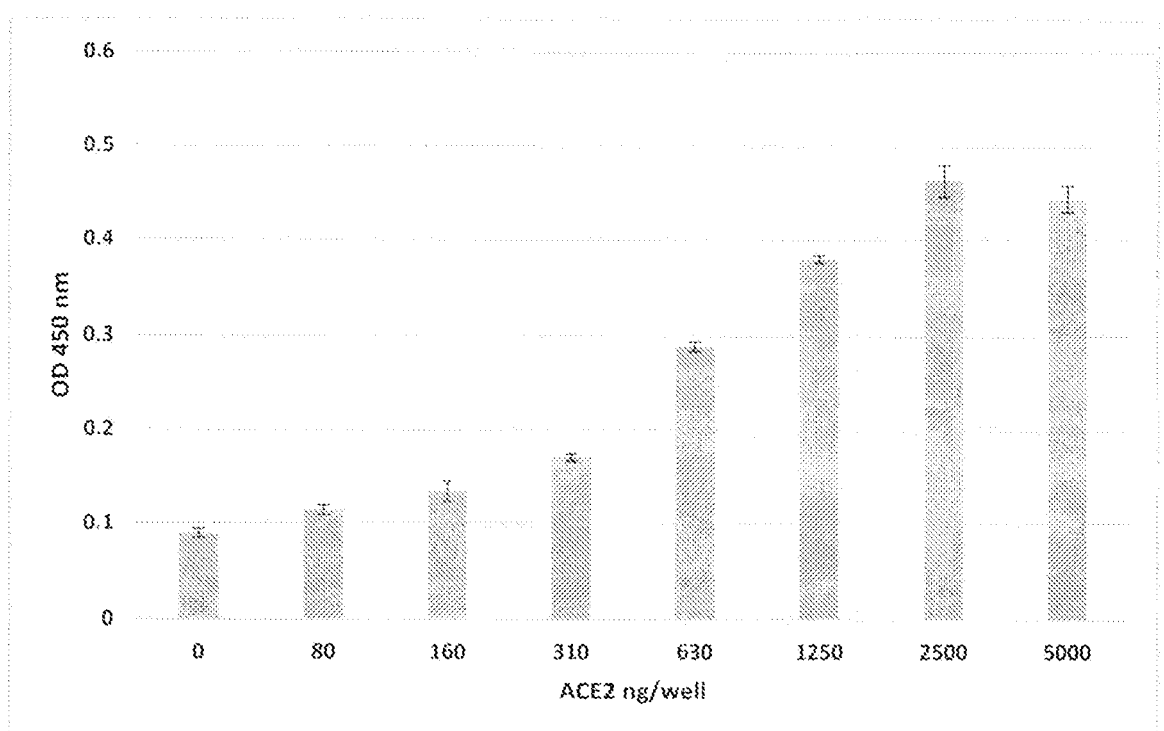
FIG. 2 is a bar graph showing the surprisingly sensitivity when the concentration of a SARS-CoV-2 Spike protein is held constant, while changing the concentration of ACE2.

Once an optimal concentration of Spike protein was selected (1.5 µg/well), the second experiment was conducted. In this experiment, a series of dilutions of ACE2 protein was used to coat microtiter wells, and binding of Spike protein to ACE2 was assessed. FIG. 2 shows that when the concentration of Spike protein was held constant at 1.5 µg/well, more robust binding was detected as the concentration of ACE2 increased, and then it plateaued. A surprisingly high sensitivity of about 96% was shown in this experiment. i.e., about 80 ng of ACE2 was capable of binding about 800 ng Spike protein.

It is important to note that for the interaction between the Spike protein of SARS-CoV-2 and its host protein receptor ACE2 to be optimally studied, microtiter wells must first be coated with ACE2. Bound Spike protein is next detected. Performing the assay in reverse, i.e., coating wells with the Spike protein and then adding ACE2, places significant limitations on one's ability to study this interaction, and in doing so, does not allow one to determine if an individual is infected with the virus.

While specific embodiments have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the (device) and method described herein, which is to be given the full breadth of the appended claims and any and all equivalents thereof.

What is claimed is:

1. A method for rapid, highly specific and sensitive, detection and quantification of a virus by observing binding of a viral substrate to its host receptor protein, comprising the steps of:
   coating a plurality of microtiter wells in a microtiter plate with a host receptor protein contained in a coating buffer;
   incubating the plurality of microtiter wells overnight;
   washing the microtiter wells;
   adding a blocking solution to the plurality of microtiter wells;
   washing the plurality of microtiter wells three times;
   adding a viral substrate to the plurality of microtiter wells;
   incubating the plurality of microtiter wells for 20 minutes;
   washing the plurality of microtiter wells three times;
   adding an antibody directed against the viral substrate to the plurality of microtiter wells;
   incubating the plurality of microtiter wells for 20 minutes;
   adding a horseradish peroxidase (HRP)-conjugated antibody directed against the antibody to the plurality of microtiter wells;
   incubating the plurality of microtiter wells for 20 minutes;
   washing the plurality of microtiter wells three times;
   adding a TMB solution to the plurality of microtiter wells;
   adding a stop solution to the plurality of microtiter wells; and
   detecting the viral substrate in the microtiter wells by observing those microtiter wells that undergo a color change, or quantifying the concentration of the viral substrate by reading optical density at 450 nm, wherein the method is completed by a user in about one hour.

2. The rapid assay of claim 1, wherein the host receptor protein and the viral substrate that binds to its host receptor protein is selected from SARS-CoV-2: Spike protein and angiotensin-converting enzyme 2 (ACE2), SARS-CoV-2: Spike protein and other host protein candidates, Betacoronaviruses (lineage A):Hemagglutinin (HA) esterase and sialic acid receptors, Influenza:HA protein, sialic acid receptors and HA2; Murine hepatitis virus (MHV): Spike protein and carcinoembryonic antigen-related cell adhesion molecule 1 (CEACAM1), and Middle East respiratory syndrome (MERS): Spike protein and dipeptidyl peptidase 4 (DPP4/CD26).

3. The rapid method of claim 2, wherein the host receptor protein and the viral substrate that binds to its host receptor protein is ACE2 and SARS-CoV-2 Spike protein.

4. The rapid method of claim 1, wherein the antibody is a rabbit polyclonal antibody.

5. The rapid method of claim 1, wherein the HRP-conjugated antibody is an HRP-conjugated anti-rabbit polyclonal goat antibody.

6. The rapid method of claim 1, wherein after adding the blocking solution to the microtiter wells, the microtiter plate can be stored, after which it can be shipped to a user at another site, as the assay start time begins only when the viral substrate is added to the microtiter wells.

7. A method for rapid, highly specific and sensitive, detection and quantification of a virus in an individual suspected of being infected with a virus by observing binding of a specimen taken from the individual with a host receptor protein, comprising the steps of:

coating a plurality of microtiter wells with a host receptor protein contained in a coating buffer;
incubating the plurality of microtiter wells overnight;
washing the microtiter wells;
adding a blocking solution to the plurality of microtiter wells;
washing the plurality of microtiter wells three times;
adding a viral substrate to the plurality of microtiter wells;
incubating the plurality of microtiter wells for 20 minutes;
washing the plurality of microtiter wells three times;
adding an antibody directed against the viral substrate to the plurality of microtiter wells;
incubating the plurality of microtiter wells for 20 minutes;
adding a horseradish peroxidase (HRP)-conjugated antibody directed against the antibody to the plurality of microtiter wells;
incubating the plurality of microtiter wells for 20 minutes;
washing the plurality of microtiter wells three times;
adding a TMB solution to the plurality of microtiter wells;
adding a Stop solution to the plurality of microtiter wells; and
detecting the viral substrate in the microtiter wells by observing those microtiter wells that undergo a color change, or quantifying the concentration of the viral substrate by reading optical density at 450 nm, wherein the method is completed by a user in about one hour.

8. The rapid method of claim 7, wherein after adding the blocking solution to the microtiter wells, the microtiter plate can be stored, after which it can be shipped to a user at another site, as the assay start time begins only when the viral substrate is added to the microtiter wells.

9. The rapid method of claim 7, wherein the suspected virus is SARS-CoV-2 and the host receptor protein is ACE2.

10. The rapid method of claim 7, wherein the infection is consistent with COVID-19.

11. The rapid method of claim 7, wherein the specimen is selected from a nasopharyngeal swab, cerebrospinal fluid, amniotic fluid, serum, plasma, whole blood, bronchopulmonary lavage, nares, vaginal sampling and a rectal/stool sampling obtained from the individual.

12. The rapid method of claim 11, wherein the specimen is a nasopharyngeal swab.

13. The rapid method of claim 7, wherein the antibody is a rabbit polyclonal antibody.

14. The rapid method of claim 7, wherein the HRP-conjugated antibody is an HRP-conjugated anti-rabbit polyclonal goat antibody.

15. The rapid method of claim 7, wherein the binding of the suspected virus SARS-CoV-2 to ACE2-coated microtiter wells is studied in the presence of antibodies contained in convalescent sera or plasma obtained from individuals who have recovered from COVID-19 or from purified monoclonal antibodies.

16. The rapid method of claim 7, wherein the binding of suspected SARS-CoV-2 to ACE2-coated microtiter wells is studied in the presence of drug candidates which may compete for binding and negatively influence the interaction between the viral substrate and its receptor.

17. The rapid method of claim 16, wherein the drug candidates are selected from remdesivir and hydroxychloroquine.

18. A test kit for rapid, highly specific and sensitive, point-of-care detection of a virus in an individual suspected of being infected with a virus, comprising:
a plurality of microtiter wells in a microtiter plate, said microtiter wells coated with a host receptor protein specific for a virus deposited on surfaces of the plurality of microtiter wells;
an antibody directed against the viral substrate;
a wash liquid for washing the plurality of microtiter wells and for preparing a mixture consisting of the wash liquid, an HRP-conjugated antibody directed against the antibody, and a specimen obtained from an individual suspected being infected with the virus, said mixture made into one or more serial dilutions that are deposited atop the coating in the plurality of microtiter wells;
a TMB solution; and
a STOP solution, wherein the detection of the virus in the specimen is achieved by observing those microtiter wells that undergo a color change, said color change occurring in about five minutes and said detection accomplished by a user in about thirty minutes.

19. The test kit of claim 18, wherein the host receptor protein and the viral substrate that binds to its host receptor protein is selected from SARS-CoV-2:Spike protein and angiotensin-converting enzyme 2 (ACE2), SARS-CoV-2: Spike protein and other host protein candidates, Betacoronaviruses (lineage A):Hemagglutinin (HA) esterase and sialic acid receptors, Influenza:HA protein, sialic acid receptors and HA2; Murine hepatitis virus (MHV):Spike protein and carcinoembryonic antigen-related cell adhesion molecule 1 (CEACAM1), and Middle East respiratory syndrome (MERS): Spike protein and dipeptidyl peptidase 4 (DPP4/CD26).

20. The test kit of claim 19, wherein the suspected virus is SARS-CoV-2 and the host receptor protein is ACE2.

21. The rapid method of claim 18, wherein the specimen is selected from a nasopharyngeal swab, cerebrospinal fluid, amniotic fluid, serum, plasma, whole blood, bronchopulmonary lavage, nares, vaginal sampling and a rectal/stool sampling obtained from the individual.

22. The test kit of claim 21, wherein the specimen is a nasopharyngeal swab obtained from the individual.

23. The test kit of claim 18, wherein the antibody is a rabbit polyclonal antibody.

24. The test kit of claim 18, wherein the HRP-conjugated antibody is an HRP-conjugated anti-rabbit polyclonal goat antibody.

25. The test kit of claim 18, wherein the infection is COVID-19.

* * * * *